Feb. 2, 1965 C. H. FISCHER Plant Pat. 2,470
GLADIOLUS PLANT
Filed Nov. 8, 1963
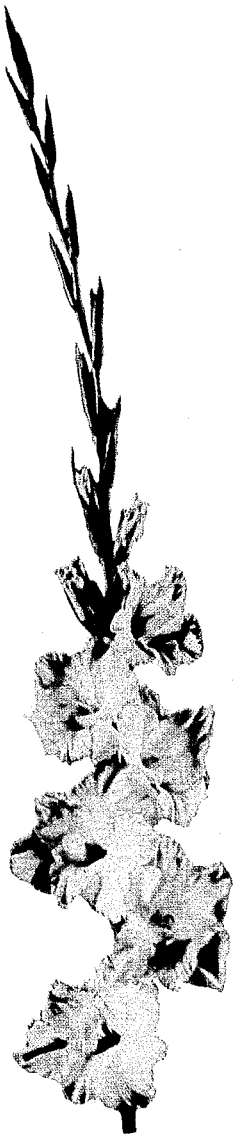
INVENTOR
Carl H. Fischer
BY Lamont Johnston
ATTORNEY United States Patent Office Plant Pat. 2,470
Patented Feb. 2, 1965

2,470
GLADIOLUS PLANT

Carl H. Fischer, St. Charles, Minn., assignor to Selected Glads, Inc., New Albany, Ind., a corporation of Tennessee Filed Nov. 8, 1963, Ser. No. 322,546
1 Claim. (Cl. Plt.—85)

My present invention relates to a new and improved variety of gladiolus plant, the blossom of which is notable particularly for its small size, beauty of form and ruffling and ability to open from tight bud.

To the best of my knowledge, this new variety is the result of a cross between the varieties Carved Ivory (unpatented) and Starlet (unpatented), Carved Ivory being the seed parent and Starlet the pollen parent. Hand cross pollination was done by me in my field at St. Charles, Minnesota, but no precaution was taken to prevent admixture of other varieties by bees or insects.

The new variety has been asexually reproduced by me in Minnesota by natural increase from cormels through several generations and its characteristics have proven to be permanently fixed.

The illustration, made a part of this application, shows a single bloom spike of this variety, reduced in size, and is as nearly true to color as it is possible to depict. The illustration shows the informal placement of the florets, the ruffling and shape of the florets and the tapering flower-head.

In the following detailed description, color plate references are to "The Horticultural Colour Chart," by The British Colour Council. Where there are other references to color, the ordinary dictionary meanings of the terms are intended.

*The plant*

Growth: Vigorous and willowy. Bloom spike averages 58 inches from large bulbs. Moderate propagator.

Blooming: The variety is an early bloomer, coming into bloom in about 75 days from large bulbs.

Stems: Straight, whippy. Diameter at base of stem is ¼ inch.

Foliage: Leaves are slender and upright; leaves are 1¼ inches wide. Plant foliage, excluding the flower spike, is 30 to 34 inches tall. Stem is white above the bulb.

Disease resistance: This variety has been found unusually resistant to Fusarium yellows, Sclerotinia dry rot and Septoria leaf spot, to which some other varieties in my fields have been subject, observed when grown as a seedling under irrigation in the black loam soil in the vicinity of St. Charles, Minnesota, under the natural conditions provided by the climate of that area.

Corms: Normal, healthy corms. Husks are thin and papery; light straw colored. Flesh of corm is Egyptian Buff $407/_1$.

*The flower*

Spike: Tall and tapering with a 20 to 24 inch flowerhead. Fourteen buds of which six open at once with five to six in color.

Bud:

*Size.*—Opening buds are 2½ inches long.

*Opening.*—Five to six will show color at one time.

Flower:

*Arrangement.*—The flowers are informally placed on the stem and always face forward.

*Size.*—Individual florets measure 3½ inches across. Upper blooms are progressively smaller.

*Form.*—Round, ruffled and widely spaced on the stem.

*Keeping qualities.*—Exceptionally good keeper.

Petals:

*Shape.*—Ruffled and recurved; outer petals are needle-pointed.

*Size.*—Outer petals are 1¾ inches across; lower petals ¾ inches.

*Aspect.*—Substance is heavy.

*Fragrance.*—None.

*Color.*—Greenish white; throat is Uranium Green $63/_3$ shading to $63/_2$ at calyx and in the opening florets.

Reproductive organs:

*Stamens.*—White.

*Pistil.*—White.

*Comparisons*

My new variety resembles Starlet (unpatented) more than any other variety, but differs from it principally as follows:

(1) My variety is more ruffled.
(2) My variety opens more florets at one time.
(3) My variety has a greener throat.
(4) My variety opens better from tight bud.

Having thus disclosed my invention, I claim:

The new and distinct variety of gladiolus plant, substantially as herein shown and described, the blossom being characterized by its small size, beauty of form and ruffling and ability to open from tight bud.

No references cited.

ABRAHAM G. STONE, *Primary Examiner.*